United States Patent [19]

Krass

[11] Patent Number: 4,657,580

[45] Date of Patent: * Apr. 14, 1987

[54] HERBICIDALLY ACTIVE SUBSTITUTED DIPHENYL ETHER OXIME DERIVATIVES

[75] Inventor: Dennis K. Krass, Canal Fulton, Ohio

[73] Assignee: PPG Industries, Inc., Pittsburgh, Pa.

[*] Notice: The portion of the term of this patent subsequent to Jan. 14, 2003 has been disclaimed.

[21] Appl. No.: 809,380

[22] Filed: Dec. 16, 1985

Related U.S. Application Data

[60] Continuation-in-part of Ser. No. 695,500, Jan. 28, 1985, Pat. No. 4,564,385, which is a continuation-in-part of Ser. No. 373,815, Apr. 30, 1982, abandoned, which is a division of Ser. No. 136,171, Apr. 15, 1980, Pat. No. 4,344,789, which is a continuation-in-part of Ser. No. 38,043, May 11, 1979, abandoned.

[51] Int. Cl.$^4$ ............................................. A01N 37/42

[52] U.S. Cl. ........................................ 71/98; 71/108; 71/105; 71/115; 562/426; 562/435; 562/440; 560/21; 560/35; 560/15; 558/422; 558/424

[58] Field of Search ............... 562/435, 426, 440; 560/21, 35, 15; 558/422, 424; 71/98, 108, 105, 115

[56] References Cited

U.S. PATENT DOCUMENTS 4,564,385 1/1986 Krass ........................................ 71/98

Primary Examiner—James H. Reamer
Attorney, Agent, or Firm—Edward J. Whitfield

[57] ABSTRACT

This invention relates to certain herbicidally active substituted diphenyl ether oxime derivatives, herbicidal compositions of the same and the use thereof for pre-emergence and postemergence control of noxious plants, i.e., weeds.

4 Claims, No Drawings

HERBICIDALLY ACTIVE SUBSTITUTED DIPHENYL ETHER OXIME DERIVATIVES

CROSS-REFERENCE TO RELATED APPLICATIONS

This application is a continuation-in-part of copending application Ser. No. 695,500 filed Jan. 28, 1985 now U.S. Pat. No. 4,564,385 which is a continuation-in-part of copending application Ser. No. 373,815, filed Apr. 30, 1982 now abandoned, which is a division of application Ser. No. 136,171 filed Apr. 15, 1980, now U.S. Pat. No. 4,344,789, which is a continuation-in-part of application Ser. No. 38,043 filed May 11, 1979, since abandoned.

FIELD OF THE INVENTION

This invention relates to certain substituted diphenyl ether oxime derivatives and to the use of same to control the growth of noxious plants, i.e., weeds.

DESCRIPTION OF THE INVENTION

This invention provides herbicidally active substituted diphenyl ether oxime compounds represented by the Formula I:

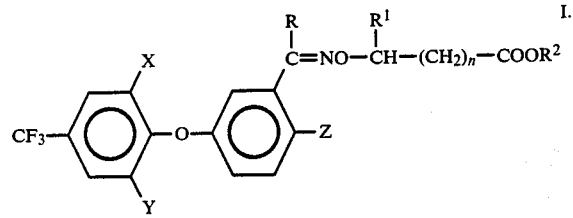

wherein:
- X and Y are the same or different halogen;
- Z is nitro, halogen or cyano;
- R is hydrogen, halogen, $C_1$ to $C_4$ alkyl or haloalkyl, $C_1$ to $C_4$ alkoxy or alkylthio, or mono or dialkylamino;
- $R^1$ is hydrogen, or $C_1$ to $C_4$ alkyl;
- $R^2$ is hydrogen or $C_1$ to $C_{10}$ alkyl, haloalkyl or alkoxyalkyl; and
- n is 0, 1, 2 or 3.

It is, of course, understood that agronomically acceptable salts of the Formula I compounds are within the scope of this invention, e.g., compounds wherein $R^2$ is an alkali metal ion, ammonium or substituted ammonium ion. Stereo and optical isomers of the Formula I compounds are also included.

Suitable alkyl radicals of which the various 'R' groups are representative include methyl, ethyl, n-propyl, iso-propyl, n-butyl, t-butyl or iso-butyl. Chloromethyl, chloroethyl, dichloroethyl, bromomethyl, bromoethyl, trifluoromethyl, trifluoroethyl, trichloromethyl and the like are exemplary haloalkyls. As examples of alkoxy and alkylthio radicals there may be mentioned methoxy, ethoxy, propoxy, methylthio, ethylthio or the like. Mono or dialkyl amino groups include methylamino, dimethylamino, methylethylamino, diethylamino or the like. Halogens represented by X, Y, and Z include bromine, chlorine or fluorine. Sodium, potassium or lithium, preferably sodium or potassium, are exemplary of alkali metal ion represented by $R^2$.

Preferred compounds of the Formula I are those wherein X and Y are fluorine or chlorine; Z is nitro or halogen; R is alkyl or haloalkyl; $R^1$ is hydrogen; $R^2$ is alkyl or haloalkyl; and n is 0.

Compounds of the Formula I may be prepared using techniques known to and starting materials available to the art. For example, a Formula I compound may be prepared by a transoximation reaction between an appropriately substituted diphenyl ether ketone or aldehyde of the Formula II:

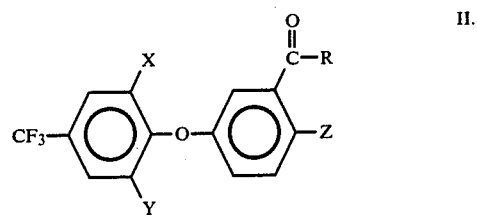

wherein X, Y, Z and R are as previously defined, with an appropriately substituted aldoxime or ketoxime-O-alkanoic acid.

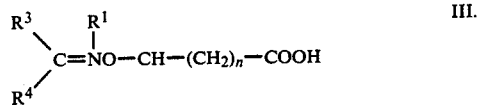

wherein $R^1$ and $R^2$ and n are as previously defined and $R^3$ and $R^4$ are hydrogen or lower alkyl. The resulting diphenyl ether oxime-O-alkanoic acid may then be esterified by reaction with a suitably substituted alcohol.

The following Example is illustrative of the preparation of a certain compound of this invention.

EXAMPLE

Preparation of: 5-(2-chloro-6-fluoro-4-trifluoromethylphenoxy)-2-nitroacetophenone oxime-O-(acetic acid, methyl ester).

(a) A reactor was charged with 10.71 grams (1.05 equiv.) of m-hydroxyacetophenone and 75 milliliters of dimethyl sulfoxide. To this stirred mixture were added 12.42 grams (1.2 equiv.) of anhydrous potassium carbonate and then 16.2 grams (1.0 equiv.) of 3,4-difluoro-5-chlorobenzotrifluoride. This stirred mixture was heated for four hours at 59° C. and then poured into a mixture of 200 milliliters of toluene and 300 milliliters of water. After phase separation, the organic phase was washed consecutively with 100 milliliters of 2 percent aqueous sodium hydroxide and 10 percent aqueous sodium chloride. The washed organic phase was dried over anhydrous magnesium sulfate, filtered and stripped of solvent affording 23.62 grams of clear, yellow oil identified by spectral analyses as 3-(2-chloro-6-fluoro-4-trifluoromethylphenoxy)acetophenone.

(b) A reactor was charged with 20 grams (1.0 equiv.) of the acetophenone, prepared as described in paragraph (a), and 55 milliliters of concentrated sulfuric acid. This stirred mixture was cooled to −10° C. and 6.48 grams (1.2 equiv.) of a V/V mixture of 70 percent nitric acid, 29 percent sulfuric acid and 1.0 percent water was added over a period of 50 minutes, the temperature rising to 0° C. over the addition period. After stirring for one hour at 0° C. to −12° C., the mixture was poured into 500 grams of ice and extracted with 500 milliliters of methylene chloride. After phase separation, the organic phase was washed consecutively with 500 milliliters of water, 250 milliliters of 2 percent aqueous sodium hydroxide and 500 milliliters of water. The washed organic phase was dried over anhydrous magnesium sulfate, filtered and stripped of solvent affording 21.53 grams of tan solid which HPLC analysis showed to be a mixture (77.8 area %, 15.9 area %) of two major products. The solid was recrystalized in 100 milliliters of 95 percent ethanol affording 15.32 grams of a crystalline solid (melting at 118°–123° C., 99.1% purity) identified by spectral analyses as 5-(2-chloro-6-fluoro-4-trifluoro-methylphenoxy)-2-nitroacetophenone.

(c) A reactor was charged with 14.0 grams (1.0 equiv.) of the 2-nitroacetophenone, prepared as described in paragraph (b), 4.86 grams (1.2 equiv.) of aminooxyacetic acid.hemihydrochloride and 140 milliliters of methanol. The mixture was refluxed for about 6 hours and an additional 0.77 gram (0.2 equiv.) of aminooxyacetic acid.hemihydrochloride was added. After refluxing an additional 18 hours, the mixture was stripped of solvent and the residue was dissolved in 200 milliliters of methylene chloride. This solution was washed consecutively with 2 percent aqueous sodium hydroxide and 5 percent aqueous sodium chloride then dried over anhydrous magnesium sulfate. Filtration and removal of solvent afforded 16.92 grams of an orange-yellow oil which crystallized on standing (m.p. 85°–89° C.) identified by spectral analysis as the desired product, 5-(2-chloro-6-fluoro-4-trifluoromethylphenoxy)-2-nitroacetophenone oxime-O-(acetic acid, methyl ester).

Although preparation of a certain compound of the invention has been illustrated by the foregoing example, it is to be understood that other compounds of the invention may be readily prepared by those skilled in the art using the same or similar techniques and by varying the choice of starting materials.

Some examples of such other compounds of the invention are 5-(2,6-dichloro-4-trifluoromethylphenoxy)-2-nitroacetophenone oxime-O-(acetic acid, methyl ester); 5-(2,6-difluoro-4-trifluoromethylphenoxy)-2-nitroacetophenone oxime-O-(acetic acid, methyl ester); 5-(2-chloro-6-fluoro-4-trifluoromethylphenoxy)-2-nitroacetophenone oxime-O-(propionic acid, methyl ester); 5-(2,6-difluoro-4-trifluoromethylphenoxy)-2-nitroacetophenone oxime-O-(propionic acid, methyl ester); 5-(2,6-dichloro-4-trifluoromethylphenoxy)-2-nitroacetophonenon oxime-O-(propionic acid, methyl ester) and the like.

Weed control in accordance with this invention is effected by application, either before or after emergence of weeds, of a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, less than one pound per acre of a compound of this invention would be expected to provide satisfactory weed control, although in some instances application rates in excess of one pound per acre; e.g., up to 5 or more pounds per acre might be required. Of course, the efficacy of a paticular compound against a particular weed species may readily be determined by routine laboratory or field testing in a manner well known to the art. It is expected that satisfactory weed control can be had at a rate of application in the range of 0.01 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Society of America*, may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

The compound prepared as described in the Example was tested for herbicidal efficacy, against a variety of broadleaf and grassy weed species, under controlled laboratory conditions of light, humidity and temperature. A solvent solution of said compound was applied, both preemergence and postemergence, to test flats containing the various weed species, and herbicidal efficacy was determined by periodic visual inspection, after application of the compounds. Herbicidal efficacy was determined on a Numerical Injury Rating scale of from 0 (no injury) to 10 (all plants dead).

A NIR of 7 to 9 indicates sever injury; a NIR of 4 to 6 indicates moderate injury, i.e. plant growth is reduced to the extent that normal growth would be expected only under ideal conditions; and a NIR of 1 to 3 indicates slight injury.

The following table gives the preemergence and postemergence NIR for the compound prepared as described in the Example against each of the broadleaf and grassy weed species to which it was applied. The compound was applied at a rate of 0.5 pound per acre and the NIR was determined three weeks after application.

The broadleaf (BL) weeds used in the test were coffeeweed (COFE), jimsonweed (JMWD), tall morningglory (MNGY), teaweed (TEAW), velvetleaf (VTLF), sicklepod (SKPD) and lambsquarter (LMBQ). The grassy weeds used in the test were barnyardgrass (BNGS), Johnsongrass (JNGS), wild oats (WOAT) and yellow foxtail (YLFX).

|  | NIR | |
|---|---|---|
|  | Preemergence | Postemergence |
| BL-Weeds: |  |  |
| COFE | 10 | 10 |
| JMWD | 9 | 10 |
| MNGY | 10 | 10 |
| TEAW | 10 | 10 |
| VTLF | 8 | 10 |
| SKPD | 7 | 10 |
| LMBQ | 10 | — |
| Average BL NIR | 9.1 | 10 |
| GR-Weeds: |  |  |
| BNGS | 8 | 10 |
| JNGS | 2 | 8 |
| WOAT | 2 | 10 |
| YLFX | 9 | 10 |
| Average GR NIR | 5.2 | 9.5 |

Basis these screening tests, compounds of this invention can be effectively used for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle and the like. Also controlled by the compounds of this invention are perennials such as quackgrass, Johnsongrass, Canada thistle, curly dock, filed chickweed, dandelion, Russian knapweed aster, horsetail ironweed, sesbania, cattail, wintercress, horsenettle, nutsedge, milkweed, sicklepod, and the like.

Also from the preliminary screening results it is believed that certain of the compounds of the invention, particularly the haloalkyl esters, have improved selectivity and soil persistence. In addition, the invention compounds could be used to effectively control weeds growing amongst crops such as wheat, oats, rice, barley, corn, soybeans, rice, peanuts and the like without causing significant damage to the growing crop.

Although the invention has been described in considerable detail by the foregoing, it is to be understood that many variations may be made therein by those skilled in the art without departing from the spirit and scope thereof as defined by the appended claims.

I claim:

1. A compound of the formula:

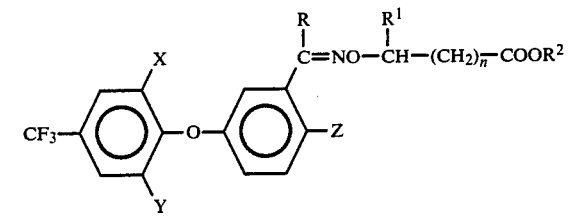

wherein:
X and Y are the same or different halogen selected from flourine or chloride;
Z is nitro, halogen or cyano;
R is hydrogen, halogen, $C_1$ to $C_4$ alkyl or haloalkyl, $C_1$ to $C_4$ alkoxy or alkylthio, or mono or dialkylamino;
$R^1$ is hydrogen, or $C_1$ to $C_4$ alkyl;
$R^2$ is hydrogen or $C_1$ to $C_{10}$ alkyl, haloalkyl or alkoxyalkyl; and
n is 0, 1, 2 or 3.

2. A compound of claim 1 wherein Z is nitro or halogen; R is alkyl or haloalkyl; $R^1$ is hydrogen; $R^2$ is alkyl or haloalkyl; and n is 0.

3. A herbicidal formulation containing an inert carrier and a herbicidally effective amount of a compound or mixture of compounds defined in claim 1.

4. In a method of controlling weeds wherein a herbicidally effective amount of herbicide is applied to a growth medium prior to emergence of the weeds therefrom or to the weeds subsequent to their emergence from the growth medium, wherein the improvement resides in using as the herbicide a compound or mixture of compounds defined by claim 1.

* * * * *